(12) United States Patent
Kuroda et al.

(10) Patent No.: US 8,993,832 B2
(45) Date of Patent: Mar. 31, 2015

(54) ABSORBENT ARTICLE HAVING COMPRESSED GROOVES

(75) Inventors: Kenichiro Kuroda, Kanonji (JP); Yuki Noda, Kanonji (JP); Shinpei Komatsu, Kanonji (JP); Osamu Nakajima, Kanonji (JP)

(73) Assignee: Unicharm Corporation, Ehime (JP)

( * ) Notice: Subject to any disclaimer, the term of this patent is extended or adjusted under 35 U.S.C. 154(b) by 921 days.

(21) Appl. No.: 13/140,506
(22) PCT Filed: Dec. 24, 2009
(86) PCT No.: PCT/JP2009/071857
§ 371 (c)(1),
(2), (4) Date: Aug. 11, 2011
(87) PCT Pub. No.: WO2010/074317
PCT Pub. Date: Jul. 1, 2010

(65) Prior Publication Data
US 2011/0288514 A1    Nov. 24, 2011

(30) Foreign Application Priority Data
Dec. 25, 2008    (JP) ................................. 2008-331164

(51) Int. Cl.
*A61F 13/533*    (2006.01)
*A61F 13/47*    (2006.01)
(Continued)

(52) U.S. Cl.
CPC ........... *A61F 13/4704* (2013.01); *A61F 13/533* (2013.01); *A61F 13/47245* (2013.01); *A61F 13/4756* (2013.01)
USPC ......................................... 604/380; D24/124

(58) Field of Classification Search
CPC ............ A61F 13/4704; A61F 13/4756; A61F 13/49001; A61F 13/533; A61F 2013/53734
USPC ........................ 604/380; D24/125, 124, 126
See application file for complete search history.

(56) References Cited

U.S. PATENT DOCUMENTS 3,881,490 A * 5/1975 Whitehead et al. ........... 604/366
D274,362 S * 6/1984 Whitehead ................... D24/125
(Continued)

FOREIGN PATENT DOCUMENTS

EP    0483592 A1    5/1992
EP    0852938 A2    7/1998
(Continued)

OTHER PUBLICATIONS

Office Action corresponding to Eurasian application No. 201100818, dated Apr. 12, 2013.
(Continued)

*Primary Examiner* — Melanie Hand
*Assistant Examiner* — Paula L Craig
(74) *Attorney, Agent, or Firm* — Lowe Hauptman & Ham, LLP

(57) ABSTRACT

Described is an absorbent article that includes at least a liquid-permeable sheet, a liquid-impermeable sheet, and an absorption body sandwiched between the liquid-permeable sheet and the liquid-impermeable sheet. A pair of right and left compressed grooves are formed along the longitudinal direction. Each compressed groove is separated into a right or left compressed groove located in the longitudinal side edge part at least in the center region of the absorption body, a front-side compressed groove located in the longitudinal front part of the side edge part, and a rear-side compressed groove located in the longitudinal rear part of the side edge part and out of these compressed grooves. The compressed groove located on the widthwise innermost side is formed to allow its end part in the separation portion to run in parallel with the longitudinal centerline or face outwardly in the width direction.

9 Claims, 7 Drawing Sheets

(51) Int. Cl.
*A61F 13/472* (2006.01)
*A61F 13/475* (2006.01)

(56) References Cited

U.S. PATENT DOCUMENTS

| | | | |
|---|---|---|---|
| D276,073 S * | 10/1984 | Whitehead | D24/125 |
| D276,183 S * | 10/1984 | Whitehead | D24/125 |
| 4,773,905 A * | 9/1988 | Molee et al. | 604/378 |
| D350,200 S * | 8/1994 | Gerhartl | D24/125 |
| 5,795,345 A * | 8/1998 | Mizutani et al. | 604/380 |
| D398,397 S * | 9/1998 | Raidel | D24/125 |
| D425,986 S * | 5/2000 | Velazquez et al. | D24/125 |
| 6,306,123 B1 * | 10/2001 | Salerno et al. | 604/385.31 |
| 6,394,989 B2 * | 5/2002 | Mizutani | 604/385.01 |
| D461,242 S * | 8/2002 | Brisebois et al. | D24/125 |
| D461,893 S * | 8/2002 | Gannon et al. | D24/125 |
| 6,506,961 B1 * | 1/2003 | Levy | 604/380 |
| D473,302 S * | 4/2003 | Harriz et al. | D24/125 |
| 6,563,013 B1 * | 5/2003 | Murota | 604/380 |
| D503,230 S * | 3/2005 | Christianson et al. | D24/125 |
| D614,766 S * | 4/2010 | Hernandez | D24/125 |
| 2001/0007065 A1 * | 7/2001 | Blanchard et al. | 604/369 |
| 2001/0039406 A1 * | 11/2001 | Hamajima et al. | 604/367 |
| 2002/0128622 A1 * | 9/2002 | Carvalho et al. | 604/385.01 |
| 2003/0018314 A1 * | 1/2003 | Nozaki et al. | 604/385.101 |
| 2003/0100874 A1 * | 5/2003 | DeCarvalho et al. | 604/380 |
| 2004/0064120 A1 * | 4/2004 | Berba et al. | 604/380 |
| 2004/0176734 A1 * | 9/2004 | Rasmussen et al. | 604/380 |
| 2004/0243082 A1 * | 12/2004 | Kinoshita et al. | 604/380 |
| 2004/0267220 A1 * | 12/2004 | Hull et al. | 604/380 |
| 2005/0124951 A1 * | 6/2005 | Kudo et al. | 604/380 |
| 2005/0148971 A1 * | 7/2005 | Kuroda et al. | 604/380 |
| 2005/0148973 A1 * | 7/2005 | Tamura et al. | 604/380 |
| 2006/0058761 A1 * | 3/2006 | Kudo et al. | 604/380 |
| 2006/0116653 A1 * | 6/2006 | Munakata et al. | 604/380 |
| 2006/0276767 A1 | 12/2006 | Ueminami et al. | |
| 2007/0073253 A1 * | 3/2007 | Miyama et al. | 604/380 |
| 2008/0065037 A1 * | 3/2008 | Konawa | 604/378 |
| 2008/0281287 A1 * | 11/2008 | Marcelo et al. | 604/383 |
| 2010/0069874 A1 * | 3/2010 | Noda et al. | 604/385.23 |
| 2011/0251575 A1 * | 10/2011 | Kuroda et al. | 604/380 |
| 2013/0123729 A1 * | 5/2013 | Minami et al. | 604/380 |
| 2013/0211360 A1 * | 8/2013 | Hashino et al. | 604/380 |

FOREIGN PATENT DOCUMENTS

| | | |
|---|---|---|
| EP | 1332742 A1 | 8/2003 |
| JP | 2-88625 U | 7/1990 |
| JP | 10-272155 A | 10/1998 |
| JP | 2002-65741 A | 3/2002 |
| JP | 2003-265519 A | 9/2003 |
| JP | 2005-177078 A | 7/2005 |
| JP | 2007-195665 A | 8/2007 |
| JP | 2008-80150 A | 4/2008 |
| JP | 2008-295475 A | 12/2008 |
| WO | 0032145 A1 | 6/2000 |
| WO | 0207663 A1 | 1/2002 |
| WO | 2004078085 A1 | 9/2004 |
| WO | 2006130646 A1 | 12/2006 |

OTHER PUBLICATIONS

International Search Report for PCT/JP2009/071857 mailed Apr. 20, 2010.
Extended European Search Report with English translation for PCT/JP2009/071857 mailed Feb. 1, 2013.
Chinese Office Action with English translation dated Jan. 21, 2013.
Japanese Office Action with English translation dated Oct. 30, 2012.

* cited by examiner

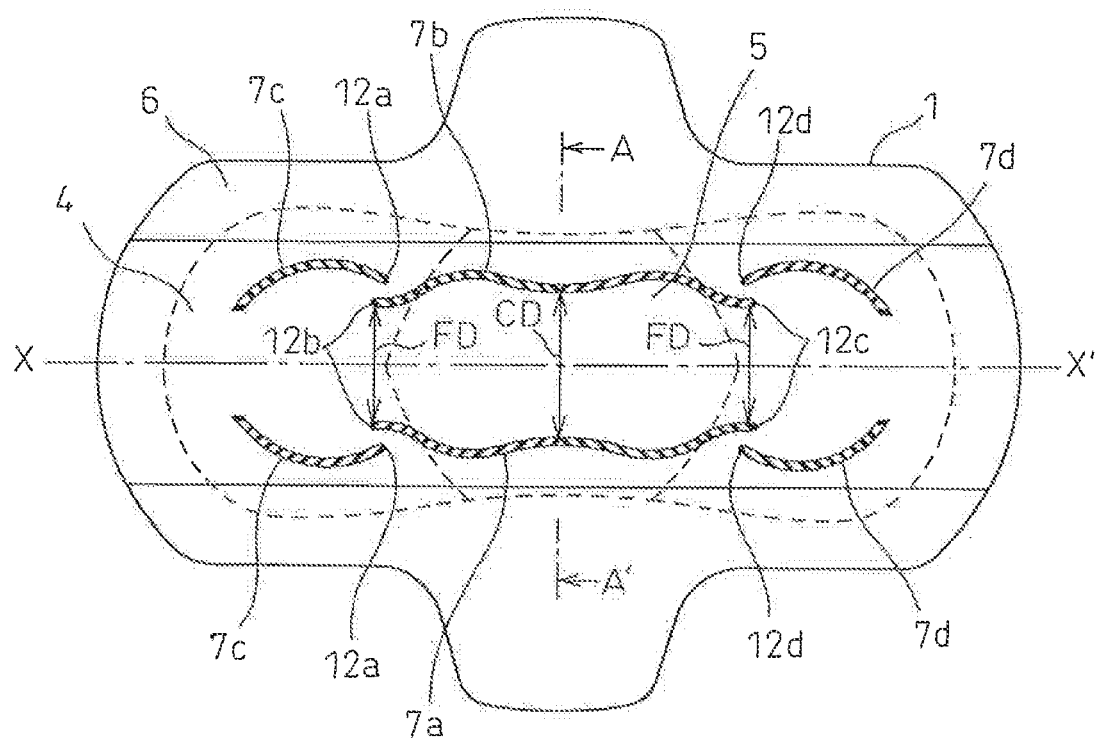

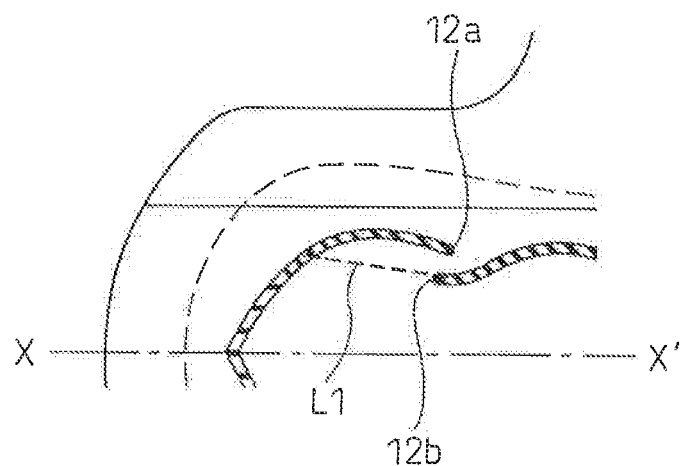
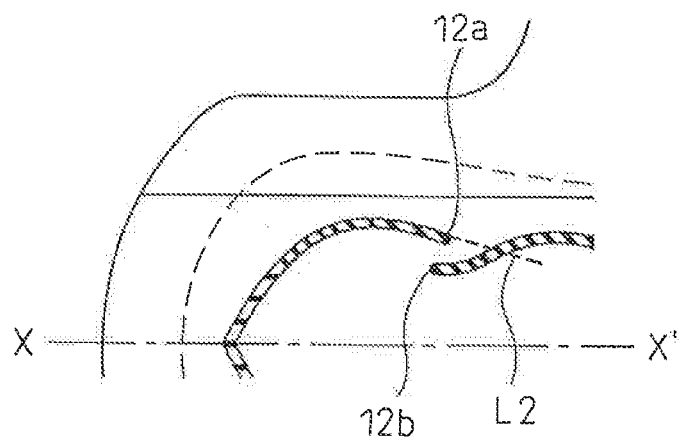

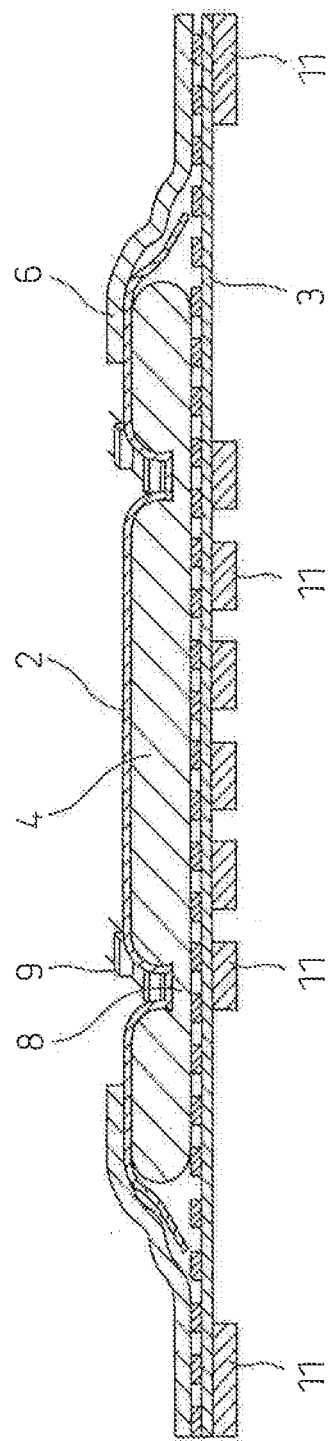

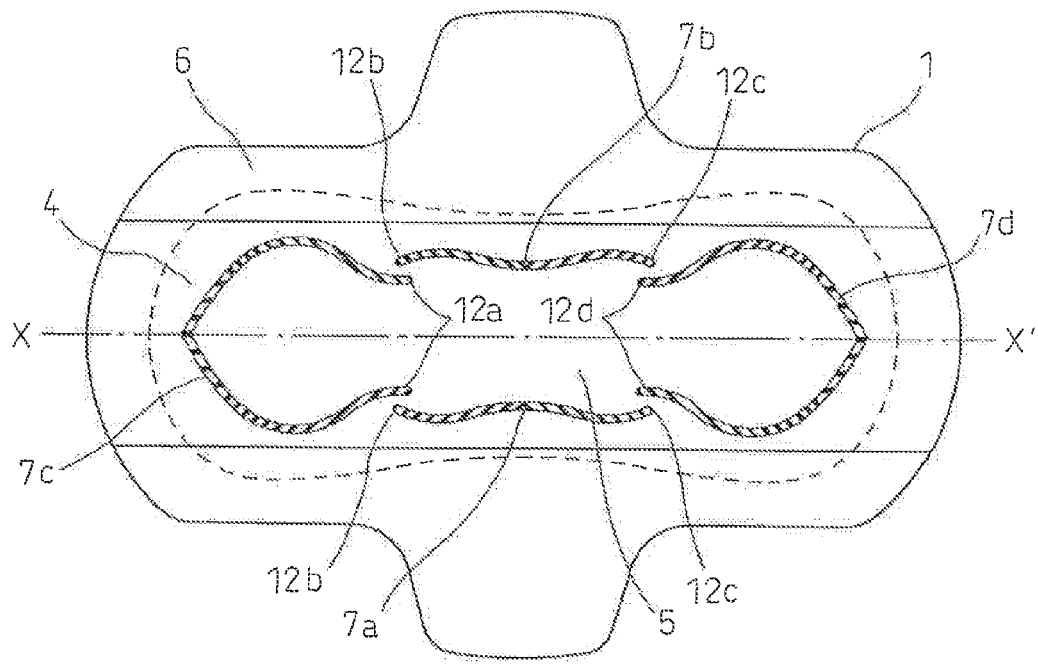
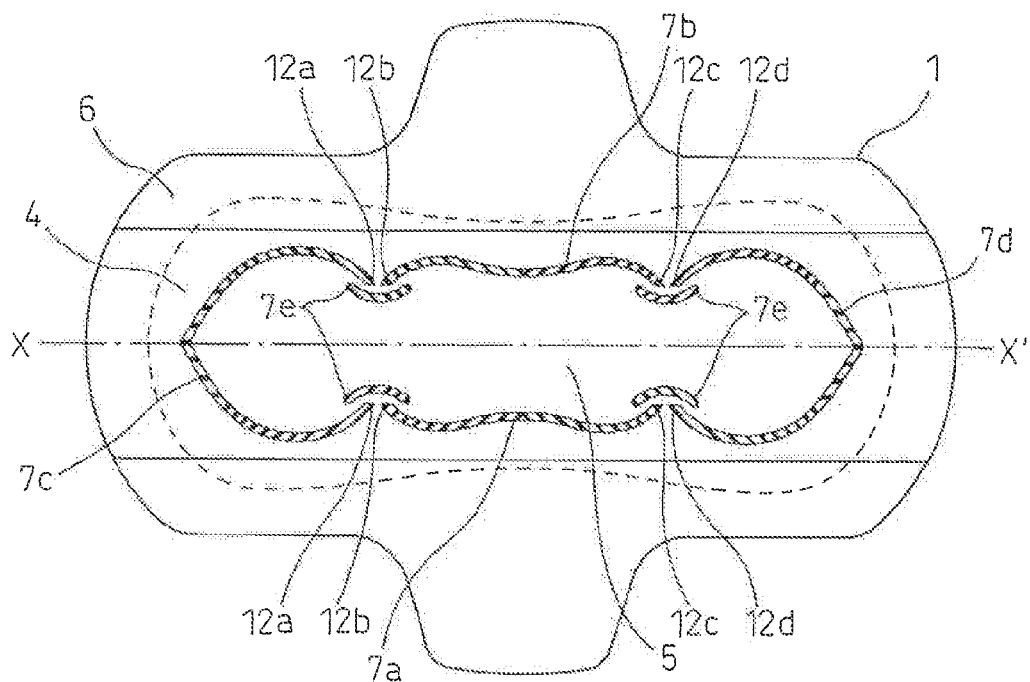

ABSORBENT ARTICLE HAVING COMPRESSED GROOVES

RELATED APPLICATIONS

The present application is a National Phase of International Application Number PCT/JP2009/071857, filed Dec. 24, 2009 and claims priority from, Japanese Application Number 2008-331164, filed Dec. 25, 2008.

TECHNICAL FIELD

The present invention relates to an absorbent article used for sanitary napkins, pantiliners, incontinence pads and the like, which is enhanced in comfort and absorptivity thanks to deformation of the absorbent article during wearing.

BACKGROUND ART

Japanese Unexamined Patent Publication (Kokai) No. 2007-195665 discloses an absorbent article having, on the skin-contact surface side of the absorbing layer, convexly curved grooves which are paired on the longitudinal front and rear sides and paired on the right and left sides along the longitudinal direction. In this absorbent article, the front end part of the left groove and the front end part of the right groove are located more on the longitudinal front side than the rear end part of the front groove. Therefore, so-called virtual extended lines obtained by extending the left groove and the right groove toward the longitudinal centerline direction, intersect on the longitudinal centerline to form a nearly V-shaped fold line.

Usually, a force is imposed on the right and left grooves from leg openings during wearing of the absorbent article (a force is imposed in the Y region of FIG. 7), and the force is transmitted to the direction close to the longitudinal centerline of the groove. In the absorbent article of Kokai No. 2007-195665, the right and left grooves are formed to allow their front and rear ends to extend toward the longitudinal centerline and at the same time, the rear ends are closer to the longitudinal centerline than to the position corresponding to a body fluid discharge port, which brings about excessive concentration of the force on this point, as a result, the absorption body on the longitudinal centerline forms a bulge part on the skin-contact surface side and the shape formed by connecting the bulge part and the front or rear end parts of the right and left grooves is liable to change into a projection. The projection may rub the skin to give an uncomfortable feeling during wearing or the liquid excrement may readily roll down on the slant face of the projection and spread to cause leakage.

SUMMARY OF THE INVENTION

An object of the present invention is to provide an absorbent article enhanced in comfort and absorptivity for a liquid excrement by deformation of a specific absorbent article during wearing.

Under these circumstances, the present inventors have made intensive studies, as a result, it has been found that when a pair of right and left compressed grooves are disposed along the longitudinal direction on the skin-contact surface side of the absorbent article and each compressed groove is separated into a longitudinal side edge part at least in the center region of the absorption body, a longitudinal front part of the side edge part, and a longitudinal rear part of the side edge part and when out of these compressed grooves, the compressed groove located on the widthwise innermost side is formed to allow its end part in the separation portion to run in parallel with the longitudinal centerline or face outwardly in the width direction, a bulge part of the desired shape rising toward the skin-contact surface side is formed and the above-described object can be thereby attained. The present invention has been accomplished based on this finding.

Hereinafter, the term "bulge part" as used herein indicates a portion formed on the skin-contact surface side of an absorbent article after a force is imposed on the right and left compressed grooves (a force is imposed on the region Y of FIG. 7) during wearing of the absorbent article and the force is transmitted toward the direction close to the longitudinal centerline, and its shape is not a projection as described in Kokai No. 2007-195665, but is a gentle convex.

That is, (1) the present invention provides an absorbent article comprising at least a liquid-permeable sheet, a liquid-impermeable sheet, and an absorption body sandwiched between the liquid-permeable sheet and the liquid-impermeable sheet, wherein a pair of right and left compressed grooves are formed along the longitudinal, direction on the skin-contact surface side of the absorbent article, each compressed groove is separated into a right or left compressed groove located in the longitudinal side edge part at least in the center region of the absorption body, a front-side compressed groove located in the longitudinal front part of the side edge part, and a rear-side compressed groove located in the longitudinal rear part of the side edge part and out of these compressed grooves, the compressed groove located on the widthwise innermost side is formed to allow its end part in the separation portion so as to run in parallel with the longitudinal centerline or face outwardly in the width direction.

(2) The present invention provides the absorbent article according to (1), wherein widthwise overlap of end parts is provided between the right or left compressed groove and the front-side compressed groove and between the right or left compressed groove and the rear-side compressed groove.

(3) The present invention provides the absorbent article according to (1) or (2), wherein the distance between right and left compressed grooves at the position corresponding to a body fluid discharge port is larger than the distance between front end parts of the right and left compressed grooves or the distance between rear end parts of the right and left compressed grooves.

(4) The present invention provides the absorbent article according to any one of (1) to (3), wherein a transverse compressed groove traversing the longitudinal centerline is provided between front end parts of the right and left compressed grooves and/or between rear end parts of the right and left compressed grooves.

(5) The present invention provides the absorbent article according to any one of (1) to (4), wherein the transverse compressed groove is provided between the front-side compressed grooves and between the rear-side compressed grooves and the rigidity of the compressed groove part provided between the rear-side compressed grooves is lower than the rigidity of the compressed groove part provided between the front-side compressed grooves.

(6) The present invention provides the absorbent article according to any one of (1) to (5), wherein the front-side compressed groove and the rear-side compressed groove are connected to form a convex curve outwardly in the longitudinal direction.

(7) The present invention provides the absorbent article according to any one of (1) to (6), wherein a plurality of point-like compressed parts are disposed at intervals in the region almost surrounded by the right and left compressed grooves, the front-side compressed groove and the rear-side compressed groove.

(8) The present invention provides the absorbent article according to any one of (1) to (7), wherein all of the compressed grooves consist of a high-compressed part and a low-compressed part and the high-compressed part is composed of transverse high-compressed part regions formed to almost fully traverse the compressed groove in the widthwise direction and disposed at intervals in the longitudinal direction of the compressed groove and non-transverse high-compressed part regions formed not to traverse the compressed groove and disposed at intervals between the regions above.

(9) The present invention provides the absorbent article according to any one of (1) to (8), wherein the low-compressed part is formed to continue in the longitudinal direction of the compressed groove between transverse high-compressed part regions.

The absorbent article of the present invention is reduced in the rubbing of the absorbent article against the skin during wearing, to give almost no uncomfortable feeling, and at the same time, exhibits excellent absorptivity for a liquid excrement.

BRIEF DESCRIPTION OF THE DRAWINGS

FIG. 1 shows a plan view illustrating the first embodiment of the absorbent article of the present invention.

FIG. 1A is an enlarged view of the portion where the rear end part 12a of the front-side compressed groove and the right compressed groove 12b in FIG. 1 are overlapped. Dotted line L1 indicates the virtual extended line longitudinally extending from the front end part 12.

FIG. 1B is an enlarged view of the portion where the rear end part 12a of the front-side compressed groove and the right compressed groove 12b in FIG. 1 are overlapped. Dotted line L2 indicates the virtual extended line extending from the rear end part 12a of the front-side compressed groove toward the longitudinal centerline direction.

FIG. 3 is an A-A' cross-sectional view of the absorbent article of FIGS. 1 and 2.

FIG. 4 shows a plan view illustrating the third embodiment of the absorbent article of the present invention.

FIG. 5 shows a plan view illustrating the fourth embodiment of the absorbent article of the present invention.

MODE FOR CARRYING OUT THE INVENTION

Figure 2:
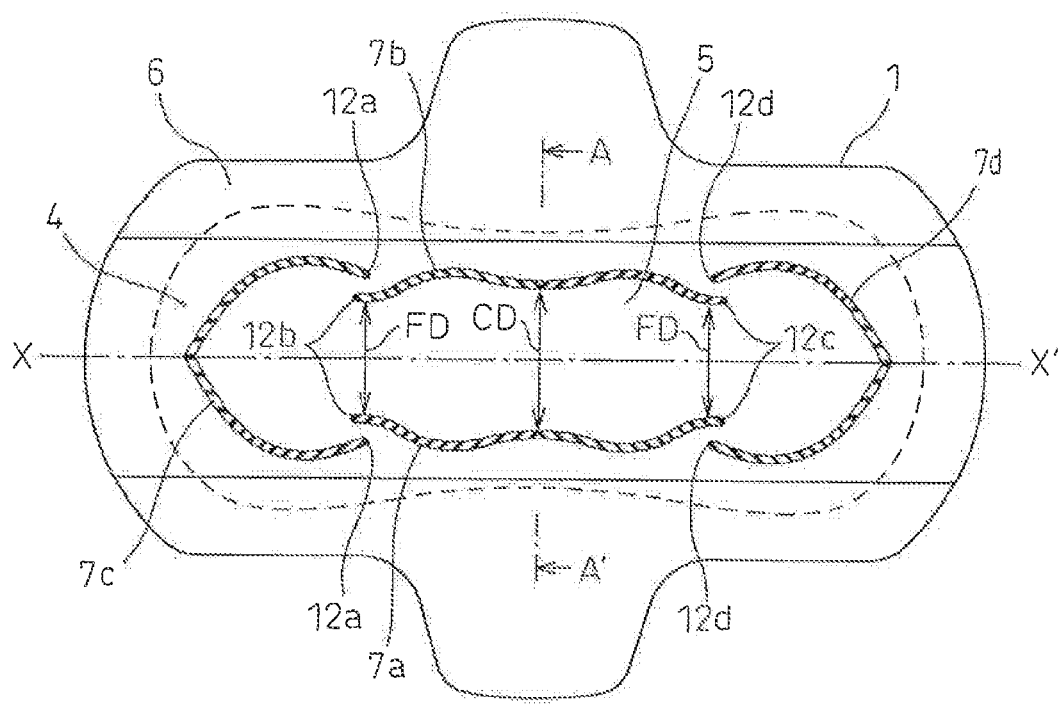
FIG. 2 shows a plan view illustrating the second embodiment of the absorbent article of the present invention.

A preferred embodiment (first embodiment) of the absorbent article of the present invention is described below by referring to the drawings.

As shown in FIGS. 1 and 3, the absorbent article 1 of the first embodiment comprises at least a liquid-permeable sheet 2, a liquid-impermeable sheet 3, and an absorption body 4 sandwiched between the liquid-permeable sheet and the liquid-impermeable sheet.

On the skin-contact surface side of the absorbent article, a pair of right and left compressed grooves 7a and 7b are formed along the longitudinal direction. The compressed groove fulfills a role of not only integrating the liquid-permeable sheet 2 and the absorption body 4 but also stopping lateral spreading of a liquid excrement from the body, such as menstrual blood and urea (hereinafter simply referred to as a "body fluid"), and allowing the body fluid to be efficiently transferred beneath the absorption body. Each compressed groove is separated into a right or left compressed groove 7a or 7b located in the longitudinal side edge part at least in the center region 5 of the absorption body, a front-side compressed groove 7c located in the longitudinal front part of the side edge part, and a rear-side compressed groove 7d located in the longitudinal rear part of the side edge part. This configuration is provided for enhancing the flexibility of the absorbent article in the longitudinal direction and avoiding such a trouble that if the right or left compressed groove 7a or 7b and the front-side compressed groove 7c are continuing, when a force is applied from leg openings, the force readily escapes also to the front-side compressed groove direction or the rear-side compressed groove direction and a bulge part is not successfully formed.

The length of the right and left compressed grooves is, forwardly or backwardly, from 20 to 80 mm, preferably from 25 to 60 mm, from near the centerline (A-A') receiving a body fluid. If the length is less than 20 mm, the distance from the center part is too short and wetting is readily caused, whereas if it exceeds 80 mm, the force from leg opening is insufficiently transmitted and a bulge part is not successfully formed. The length from the center part does not need be the same between the front side and the rear side, and the length on the rear side may be larger.

The length from the front end part of the front-side compressed groove to the rear end part of the rear-side compressed groove may be 100 mm or more when the longitudinal length of the absorbent article is 210 mm. If the length is less than 100 mm, a force is not efficiently transmitted to the compressed groove from leg openings during walking of the wearer.

The right and left compressed grooves are located to step over the position corresponding to the excretion part, to which a force is applied from leg openings during wearing. These compressed grooves are designed to be convex inwardly in the width direction in the center part and while the distance between the right and left compressed grooves is increased in the side edge part direction as proceeds toward the front or rear direction, face each other across the longitudinal center line (X-X') near the front or rear end part.

However, the right or left compressed groove 7a or 7b located on the widthwise innermost side needs to be formed such that its front end part 12b and rear end part 12c face outwardly in the width direction or run in parallel with the longitudinal centerline. By this configuration, the bulge part formed is kept from becoming a steep projection described in Kokai No. 2007-195665, allowing for little uncomfortable feeling due to rubbing of the skin by the bulge part, and also, the convex formed in the front or rear part of the body fluid receiving port has a gentle slant face, so that the body fluid adhering on the longitudinal centerline can roll down on the slant face of the bulge part and be prevented from diffusing and its leakage can be reduced. FIG. 1 shows a configuration where the front, end part 12b and the rear end part 12c are formed to face outwardly in the width direction. In this embodiment, a straight line (virtual extended line) virtually extending to the longitudinal direction from the front end part 12b or the rear end part 12c does not intersect with the longitudinal centerline. Incidentally, in this case, the virtual extended line may be drawn along the widthwise outermost part of the compressed groove or may be drawn along the widthwise centerline of the compressed groove in the end part. FIG. 1A shows an virtual extended line (L1) longitudinally extending from the front end part 12.

The distance FD between front end parts of the right and left compressed grooves is preferably equal to the distance between rear end parts and shorter than the distance CD between right and left compressed grooves in the center part. Because, the force from leg opening is first transmitted to the center part and then transmitted therefrom to the front or rear end part toward which the distance between compressed grooves is decreased, and the force from leg openings can be concentrated in the front and rear end part directions. As a result, a higher bulge part can be formed in the front and rear parts across the center part than in the center part of the absorbent article and in turn, the body fluid received in the center part can be made to scarcely diffuse toward the front and rear directions.

The distance CD between right and left compressed grooves in the center part is preferably from 20 to 50 mm. If the distance is less than 20 mm, the absorption surface becomes narrow and leakage may occur, whereas if it exceeds 50 mm, the distance becomes larger than the width between leg openings and the force from leg openings cannot be transmitted. The difference of the distance CD between right, and left compressed grooves in the center part from the distance FD between front end parts (or rear end parts) of the right and left compressed grooves is preferably from 5 to 30 mm. If the difference is less than 5 mm, the force cannot be adequately transmitted to the front and rear end parts from the center part and a sufficient effect of making the body fluid received in the center part to scarcely diffuse toward the front and rear directions can be hardly obtained. If the difference exceeds 30 mm, the distance FD between front end parts (or the distance between rear end parts) becomes small and the desired bulge part cannot be formed in the forward or rearward part of the center part.

In the first embodiment, the distance between the right and left compressed grooves is 33 mm, and both the difference between the front-side compressed grooves and the distance between the rear-side compressed grooves are 25 mm.

The front-side compressed groove 7c and the rear-side compressed groove 7d are preferably disposed such that widthwise overlap is provided between the rear end part 12a of the front-side compressed groove 7c and the front end part 12b of the right and left compressed grooves 7a and 7b and between the front end part 12d of the rear-side compressed groove 7d and the rear end part 12c of the right and left compressed grooves 7a and 7b. Even when the body fluid is absorbed in the vicinity of the rear end part of the front-side compressed groove and in the vicinity of the front end part of the rear-side compressed groove or even when the body fluid is diffused to the width direction, the leakage is reduced, because a compressed groove is further present on the widthwise outer side.

In the first embodiment, an virtual extended line (denoted by L2 in FIG. 13) drawn in the longitudinal centerline direction from the rear end part 12a of the front-side compressed groove is designed to intersect with the vicinity of the front end part 12b of the right and left compressed grooves. The virtual extended line drawn from the front end part 12d of the rear-side compressed groove is also designed to intersect with the vicinity of the rear end part 12c of the right and left compressed grooves. Because, when a force is applied to the front-side compressed groove by walking or the like, the force is applied not only to the width direction but also to the virtual extended line direction and for allowing the force imposed on the front-side compressed groove to be easily transmitted to the front end part 12b of the right and left compressed grooves, a more deformable shape can be formed by the right and left compressed grooves. Furthermore, the extended line direction is a direction toward which the area of the portion keeping the compressed grooves apart is decreased, and therefore even when a body fluid is attached to the portion, its leakage is more difficult to occur.

The second embodiment of the absorbent article of the present invention is described below. The second embodiment is described by referring mainly to the points differing from the first embodiment, and description of the same points is omitted. Accordingly, the description of the first embodiment is appropriately applied to the second embodiment.

In the second embodiment, as shown in FIG. 2, each of a pair of front-side compressed grooves 7c and a pair of right and left rear-side compressed grooves 7d is connected to form a convex curve outwardly in the longitudinal direction so as to prevent diffusion of a fluid body.

In the third embodiment, as shown in FIG. 4, the overlapped arrangement relationship between the rear end part 12a of the front-side compressed groove 7c and the front end part 12b of the right and left compressed grooves 7a and 7b, and the overlapped arrangement relationship between the front end part 12d of the rear-side compressed groove 7d and the rear end part 12c of the right and left compressed grooves 7a and 7b, may be a relationship where the rear end part 12a and the front end part 12d are located inside the front and rear end parts 12b and 12c of the right and left compressed grooves. However, in the third embodiment, as compared with the first embodiment, the effect of preventing the body fluid received in the center part from diffusing toward the front and rear directions is slightly lower. This is because a force is applied to the rear end part of the front-side compressed groove (or the front end part of the rear-side compressed groove) at intervals from the front end part of the right and left compressed grooves (or the rearward front end part of the right and left compressed grooves) and the force applied to the rear end part of the front-side compressed groove (or the front end part of the rear-side compressed groove) readily escapes also to the front-side compressed groove direction (or rear-side compressed groove direction).

The fourth embodiment differs from the first embodiment, as shown in FIG. 5, in that the front end part 12b of the right and left compressed grooves and the rear end part 12a of the front-side compressed groove are not overlapped and the rear end part 12c of the right and left compressed grooves and the front end part 12d of the rear-side compressed groove are not overlapped. Furthermore, in the widthwise innermost side of each of the separation portion of 12b and 12a and the separation portion of 12c and 12d, a transverse compressed groove 7e traversing 12b and 12a and a transverse compressed groove 7e traversing 12c and 12d are disposed. Both of front and rear end parts of the transverse compressed groove run in parallel with the longitudinal centerline or face outwardly in the width direction. Therefore, the force applied between front and rear end parts of the right and left compressed grooves can be transmitted to the transverse compressed groove and a bulge part can be formed in the forward or rearward part of the center part of the absorbent article. In turn, similarly to the absorbent article of the first embodiment, the absorbent article of the fourth embodiment also prevents the absorbent article from being folded to form a projection near between the front and rear end parts.

Figure 6:
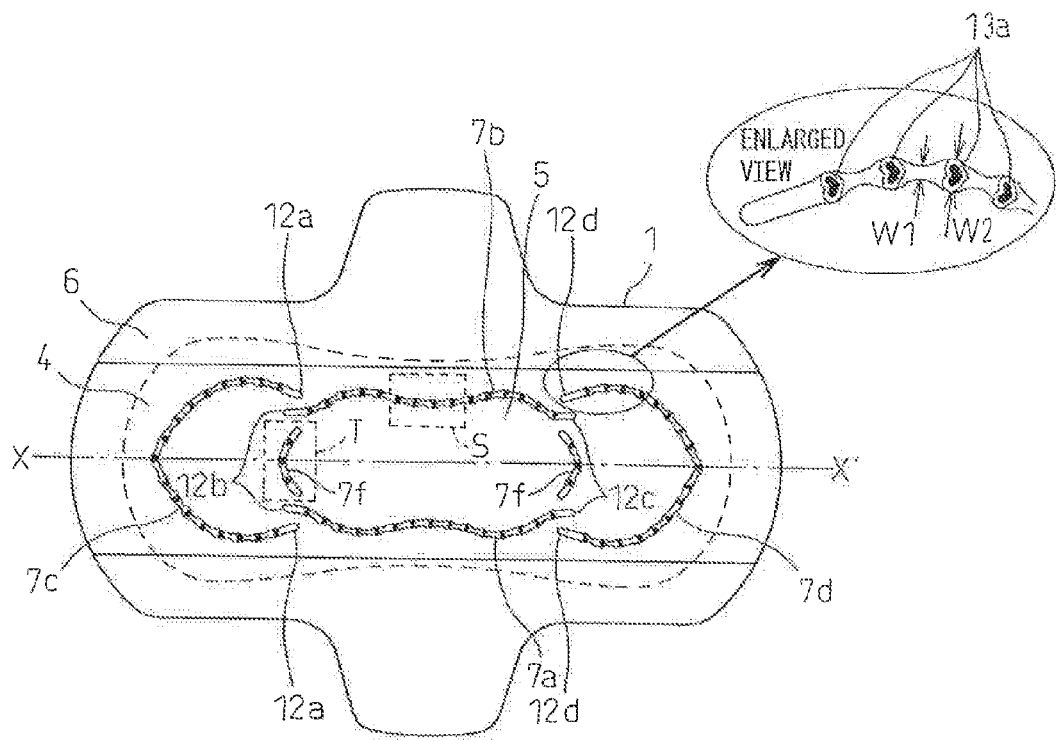
FIG. 6 shows a plan view illustrating the fifth embodiment of the absorbent article of the present invention, and an enlarged view of the compressed groove.

In the fifth embodiment, as shown in FIG. 6, a transverse compressed groove 7f traversing the longitudinal centerline is further provided between the front end parts 12b of the right and left compressed grooves and/or the rear end parts 12c of the right and left compressed grooves. Therefore, even when a large force is abruptly transmitted to the right and left compressed grooves, by virtue of the rigidity of the transverse compressed groove, the absorption body can be prevented from buckling and deforming into a projection. As for the transverse compressed groove, although the width of the absorbent article varies according to the motion during wearing, the width is restored by the repulsive force of the transverse compressed groove part and a stable absorption surface can be maintained. The transverse compressed grooves in the front and rear parts may have the same shape.

Also, in the firth embodiment, the transverse compressed groove 7f is disposed with a predetermined gap from the right and left compressed grooves, and therefore even when a force is applied to the oblique direction at different positions, that is, to the front direction of the absorbent article from the right leg during walking and to the rear direction of the absorbent article from the left leg, the absorbent article can be folded starting from the intermittent part and easily deformed even if the left or right pressure is not completely applied. Also, the gap is the same in the left and right sides of the front-side and rear-side transverse parts and even when the target wearing position is shifted or even when various postures are taken, the product can be kept flexible.

On the other hand, for causing the neighborhood of the front and rear sides of the right and left compressed grooves to convexly deform on the skin-contact surface side and thereby forming a bulge part, if the rigidity of the right and left compressed grooves is too strong, such deformation may be inhibited and this is not preferred. Accordingly, in the embodiment 5, the rigidity of the transverse compressed groove T surrounded by a dotted line of FIG. 6 is preferably from 2 to 35 mN (as measured by Gurley flexibility tester (manufactured by Yasuda Seiki Seisakusho, Ltd.)). If the rigidity is less than 2 mN, twisting is liable to occur when a large force is applied, whereas if it exceeds 35 mN, the deformation may be obstructed due to excessive hardness. The rigidity of the right and left compressed grooves surrounded by a dotted line of FIG. 6 is 12 mN, and the rigidity of the transverse compressed groove is 8 mN.

In the case where a transverse compressed groove 7f is provided between front end parts 12b of the right and left compressed grooves and the rear end parts 12c of the right and left compressed grooves, the rigidity of the transverse compressed groove in the rear part is lower than the rigidity of the transverse compressed groove in the front part. When the rigidity in the rear part is lower, the rear part is more liable to be deformed than the front part, as a result, the bulge height is higher in the rear part to enable successful fitting to the hip part.

Figure 7:
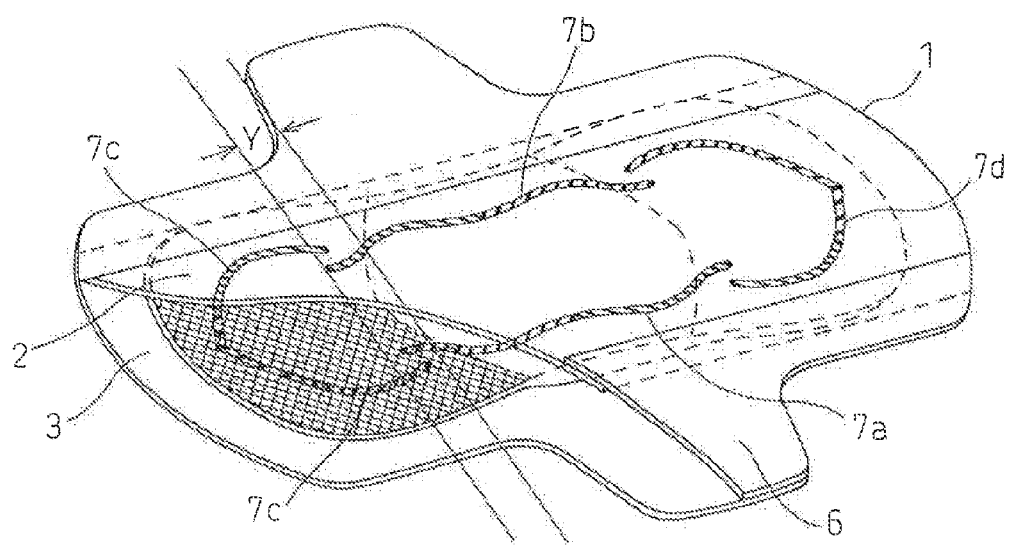
FIG. 7 shows a perspective view illustrating the sixth embodiment of the absorbent article of the present invention.

In the sixth embodiment (FIG. 7), the transverse compressed groove 7f is provided only in the absorption body (not shown), but the same effect as that of the absorbent article of the fifth embodiment is obtained.

Figure 8:
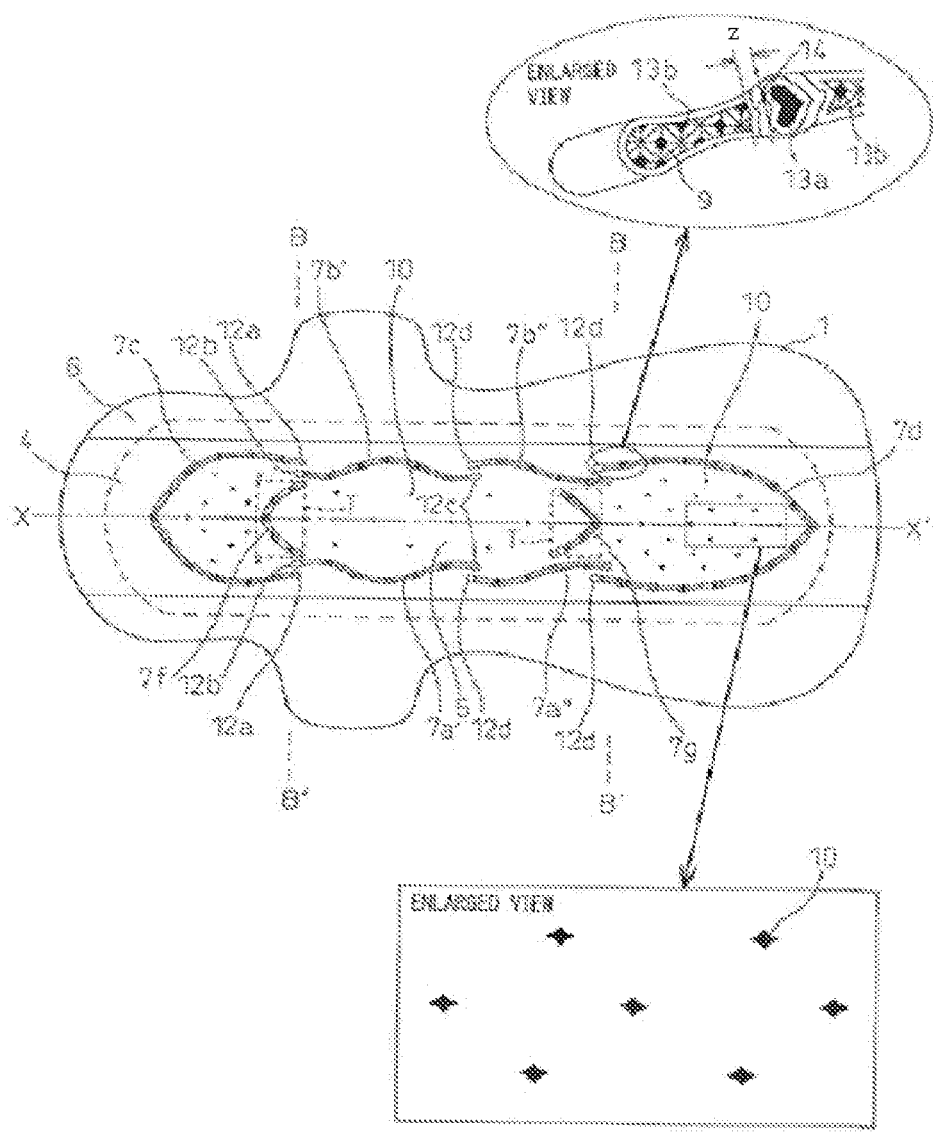
FIG. 8 shows a plan view illustrating the seventh embodiment of the absorbent article of the present invention, an enlarged view of the compressed groove, and an enlarged view of the point-like compressed part.

In the seventh embodiment, as shown in FIG. 8, each of the right and left compressed grooves 7a and 7b in FIG. 1 is further separated into two parts (7a' and 7a", and 7b' and 7b"). Out of the compressed grooves after separation into two parts, each of the right and left compressed grooves 7a' and 7b' is formed such that its front end part 12b and rear end part 12c face outwardly in the width direction or run in parallel with the longitudinal centerline.

Also, in the seventh embodiment, similarly to the fifth embodiment, transverse compressed grooves 7f and 7g are further provided, but the shape differs between the front-side and rear-side transverse compressed grooves. The front-side transverse compressed groove is in a shape of extending in the width direction, and the rear-side transverse compressed groove is in a shape of extending in the longitudinal direction and takes a more sharply-angled shape. This difference in the shape produces a difference in the rigidity of the transverse compressed groove part. That is, the rigidity of the front-side transverse compressed groove part is high as compared with the rear-side transverse compressed groove part. By providing transverse compressed grooves differing in the rigidity, a force applied to the right and left compressed grooves is transmitted to the front and rear end parts of the right and left compressed grooves, and the force is then transmitted to the rear-side transverse compressed groove having a lower rigidity, as a result, a higher bulge part than the bulge part formed between front end parts of the right and left compressed grooves is formed between rear end parts of the right and left compressed grooves.

In the seventh embodiment, the difference in rigidity is created by the shape of the front-side and rear-side transverse compressed grooves, but in the sixth embodiment above, the difference in rigidity may be created by adjusting the degree of embossing when providing front-side and rear-side transverse compressed grooves having the same shape. The difference in rigidity between front-side and rear-side transverse compressed grooves is preferably from 2 to 10 mN. If the difference is less than 2 mN, the force cannot be efficiently transmitted to the rear side, whereas if it exceeds 10 mN, the force is unevenly transmitted to one side and the absorbent article is excessively deformed.

In the seventh embodiment, the rigidity of the front-side transverse compressed groove is 10 mN, while an the rigidity of the rear-side transverse compressed groove is 7 mN. In the absorbent article of the seventh embodiment, even when the body fluid is leaked to the rearward of the hip part through the groove in the hip part at bedtime, the leakage can be stopped by the rear-side transverse compressed groove, and therefore this absorbent article is suitable for nighttime use.

The shape of the compressed groove is described below by referring to the drawings.

The compressed groove consists of, as shown in FIG. 3, a high-compressed part 8 and a low-compressed part 9 disposed alternating with the high-compressed part 8. The high-compressed part is compressed in a ratio of 50% or more based on the thickness of absorption body, and the low-compressed part is compressed in a ratio of 20% or more. By providing a high-compressed part and a low-compressed part, the joining force between the liquid-permeable sheet and the absorption body can be increased and the excrement can be collected in the high-compressed part to prevent diffusion of the excrement.

Also, as shown in FIG. 8, the high-compressed part is composed of transverse high-compressed part regions 13a formed to almost fully traverse the compressed groove in the width direction and disposed at intervals in the longitudinal direction of the compressed groove, and non-transverse high-compressed part regions 13b formed not to traverse the compressed groove and disposed at intervals between transverse high-compressed part regions.

In FIG. 8, a grid-like compressed groove part formed by the non-transverse high-compressed part region and the low-compressed part is disposed between a transverse high-compressed part region 13a and a transverse high-compressed part region 13a. In the grid-like compressed groove, since the low-compressed part is continuously formed in the groove direction, the bodily fluid flowing along the groove is easily diffused along the long direction of the compressed groove. On the other hand, the rigidity is continuous in the entire groove because the low-compressed part is continued, and therefore the rigidity is increased, along currents of the groove, but by providing a plurality of transverse parts, the rigidity of the groove is partially changed and flexibility is thereby imparted to the entire product. The shape of the high-compressed part (transverse high-compressed part region) is not particularly limited, as long as it is a shape capable of imparting flexibility by almost fully traversing the compressed groove in the width direction. For example, the shape may be, in planar view, a heart shape (FIG. 8), a diamond shape, a box shape, a triangular shape or a dot shape.

The width of the compressed groove is almost the same in the first to fourth embodiments and the sixth embodiment. On the other hand, in the fifth embodiment, as shown in the enlarged view of FIG. 6, the width (W1) of the compressed groove between a transverse high-compressed part region and a transverse high-compressed part region is preferably smaller than the width (W2) of the compressed groove where a transverse high-compressed part region is located. The same applies to the embodiment of FIG. 7 (in the enlarged view of FIG. 8, not shown). Because, the rigidity of the compressed groove between a transverse high-compressed part region and a transverse high-compressed part region can be decreased and the wearability can be more enhanced.

The distance between a transverse high-compressed part region 13a and a transverse high-compressed part region 13a is preferably from 10 to 50 mm. If the distance is less than 10 mm, the distance between high-compressed parts expanding over the entire groove width is too short and a sufficient amount of a body fluid cannot be diffused, which may allow for generation of lateral leakage. If the distance exceeds 50 mm, the rigid region is too long and the absorbent article can hardly follow the curve of the body.

In the case where the above-described grid-like compressed groove part is disposed between a transverse high-compressed part region 13a and a transverse high-compressed part region 13a, if the length of the grid-like compressed groove part is too large, the rigidity of the grid-like compressed groove part is excessively increased and this is not preferred. In such a case, for example, high-compressed part regions differing in the rigidity from each other may be provided or, as shown in the enlarged view of FIG. 8, an intermittent part 14 (low-compressed part) having a length of Z may be provided.

The point-like compressed part is described below.

On the skin-contact surface side of the absorbent article, as shown in FIG. 8, a plurality of point-like compressed parts 10 for integrating the permeable sheet and the absorption body may be disposed at constant intervals. By arranging point-like compressed parts, when a bulge part is formed in the absorbent article, a groove concaved toward the skin-contact surface side is formed on the slant face of the bulge part and the excrement attached to the top of the bulge part slides on the slant face and is absorbed in the groove without causing lateral leakage.

The point-liked compressed part is preferably disposed at least in the site near the folding position for packaging (B-B' in FIG. 8) of the absorbent article.

The shape of the point-like compressed part is not particularly limited and may be, for example, a box shape, a triangular shape, a diamond shape, a round shape or a star shape, but is preferably a diamond shape long in the longitudinal direction. Because, a point-like compressed part with a long diamond shape is liable to lift toward the skin-contact surface side when a force is applied to the right and left compressed grooves, and folding of the absorbent article is facilitated.

The width of the top-surface opening of the point-like compressed part is preferably smaller than the width of the top-surface opening of the compressed groove. Specifically, the width is from 0.3 to 5 mm, preferably from 0.5 to 3 mm, and is usually about 1.2 mm.

The distance between a compressed groove and a point-like compressed part and the distance between point-like compressed parts are 20 mm or less, preferably 15 mm or less, more preferably 10 mm or less. The depth of the point-like compressed part is preferably larger than the depth of the low-compressed part of the compressed groove.

The materials constituting the absorbent article are described below.

The absorption body may be one which absorbs and holds a body fluid, and a bulky material hardly loosing its shape and less causing chemical irritation is preferred. For example, a cellulose such as fluffed pulp and cotton, a regenerated cellulose such as rayon and fibril rayon, a semisynthetic cellulose such as acetate and triacetate, a particulate polymer, a fibrous polymer, a thermoplastic hydrophobic chemical fiber, a thermoplastic hydrophobic chemical fiber subjected to a hydrophilization treatment, and an air-laid pulp subjected to a chemical bonding treatment may be used individually or as a mixture. From the standpoint that good hydrophilicity is maintained, a cellulose fiber is preferred.

The method for forming such a material into an absorption body is not particularly limited, but other than a method of forming fluffed pulp as described in Examples 1 to 3 below, a method of forming a sheet, for example, by an air-laid process, a melt blown process, a spunlace process or a papermaking process, may be used.

As the absorption body, a cellulose foam, a continuous foam of synthetic resin, or the like may be also used. Furthermore, a foam or the above-described material shaped into sheet may be used by pulverizing and then forming it into an absorption body. Among these, an absorption body having a basis weight of 100 to 2,000 g/m$^2$ and a bulkiness of 1 to 50 mm, obtained by mixing pulp in a ratio of 80 to 100% and particulate polymer in a ratio of 20 to 0%, covering the mixture with a paper backing such as tissue paper, and forming it into a sheet by embossing, may be used.

The embossing treatment is performed to prevent the absorption body from loosing its shape, and the embossing area ratio is from 10 to 100%, preferably from 30 to 80%.

Examples of the material for a thin absorption body include an absorption sheet and a polymer sheet, and the thickness thereof is preferably from 0.3 to 5.0 mm. The absorption sheet or polymer sheet can be used without any particular limitation, as long as it is a material usually used for an absorbent article such as sanitary napkin. Examples of the absorption sheet include absorption paper, nonwoven fabric and pulp sheet obtained by forming a fiber into a sheet with a binder or the like. Examples of the polymer sheet include fluffed pulp and a sheet obtained by mixing a particulate polymer with a fiber and forming the mixture into a sheet form. In the sheet obtained by mixing a particulate polymer with a fiber and forming the mixture into a sheet form, the particulate polymer may be dispersed either in a layer form or in a three-dimensional form. The particulate polymer used for the polymer sheet is preferably a polymer capable of absorbing and holding a liquid in an amount of 20 times or more its own weight and being gelled. Examples thereof include starch, a crosslinked carboxymethylated cellulose, a polyacrylic acid and a salt thereof, and a polyacrylate graft copolymer. Also, for sufficiently maintaining the joining strength to the embossed part, as the thermoplastic chemical fiber, a fiber having high thermal adhesiveness is preferably used. When, for example, a fiber having linear PE, low-density PE, high-density PE or the like in the sheath structure or a fiber formed by incorporating PE into PP or PET, forming a sheet therefrom and dividing the sheet into strips is added, joining by heat of embossing can be more firmly maintained.

The liquid-permeable sheet is not particularly limited, as long as it is a sheet-like material having a structure allowing for permeation of a liquid. As the material for woven or nonwoven fabric, both a natural fiber and a chemical fiber can be used. Examples of the natural fiber include a cellulose such as fluffed pulp and cotton. Examples of the chemical fiber include a regenerated cellulose such as rayon and fibril rayon, a semisynthetic cellulose such as acetate and triacetate, a thermoplastic hydrophobic chemical fiber, and a thermoplastic hydrophobic chemical fiber subjected to a hydrophilization treatment.

Examples of the thermoplastic hydrophobic chemical fiber include a single fiber such as polyethylene (PE), polypropylene (PP) and polyethylene terephthalate (PET), a fiber obtained by graft copolymerization of PE and PP, and a composite fiber such as fiber having a sheath-core structure.

As the liquid-impermeable sheet, for example, a film mainly composed of PE, PP or the like, an air-permeable resin film, a sheet obtained by joining an air-permeable resin film to a nonwoven fabric such as spunbond and spunlace, or a sheet having a multilayer structure such as three-layer structure may be suitably used. Considering flexibility not impairing the wearing feel, for example, a film mainly composed of a low-density polyethylene (LOPE) resin and having a basis weight of 15 to 30 g/m$^2$ is preferably used.

A second sheet may be disposed between the liquid-permeable sheet and the absorption body. The material and production method are not particularly limited, as long as it is employed for the permeable sheet above, but for facilitating absorption of a body fluid from the liquid-permeable sheet, a second sheet more increased in the density than the liquid-permeable sheet is preferably used.

On the non-skin-contact surface of the liquid-impermeable sheet, a slip stopper 11 for fixing to an underwear such as panty is preferably provided on the non-skin-contact surface side of the liquid-impermeable sheet. The slip stopper may be continuously coated in a line or belt fashion or may be coated intermittently. Examples of the slip stopper include a hot-melt adhesive. A hot-melt adhesive having tackiness at ordinary temperature is preferred, and examples thereof include a pressure-sensitive adhesive. The adhesive has a basis weight of 10 to 200 gsm and is coated in a uniform, striped or dot pattern by coater coating, bead coating or the like. An acrylic adhesive may be also preferably used. Other examples include a member comprising a tape part and a plurality of hook parts rising on a tape part surface.

The absorbent article of the present invention can be used as a sanitary napkin, a pantiliner, an incontinence, pad or the like.

The production method of the absorbent article of the present invention includes at least an embossing step of stacking a liquid-permeable sheet 2 and an absorption body 4 and compressing the stack in the thickness direction. The compressed groove (right and left compressed grooves, front-side compressed groove, rear-side compressed groove) formed along the longitudinal side edge part of the absorbent article, the transverse compressed groove and the point-like compressed part may be simultaneously formed by the embossing or may be separately formed in any order. For example, in the case of simultaneously forming these grooves and parts, between a roll (first roll) having on the roller surface thereof convex streaks corresponding to the entire shape of these compressed grooves and convex parts corresponding to the entire shape of the point-like compressed part and a smooth roll (second roll), an absorbent material after stacking a liquid-permeable sheet and an absorption body is disposed by arranging the liquid-permeable sheet to come into contact with the first roll, and the absorbent material is compressed.

However, the absorbent article of the embodiment 6 has the transverse compressed groove only in the absorption body. Therefore, for example, the absorption body is first embossed to form a transverse compressed groove and subsequently, the absorption body and the liquid-permeable sheet are stacked and embossed to form the compressed groove formed along the longitudinal side edge part and the point-like compressed part. In this method, the transverse compressed groove is formed separately from the right and left compressed grooves, and therefore the rigidity of the right and left compressed grooves can be easily made higher than the rigidity of the transverse compressed groove by adjusting the embossing strength.

Finally, a liquid-impermeable sheet 3 is supplied to the non-skin-contact surface side of the absorption body 4 of the embossed absorbent material, and the absorption body 4 and the liquid-impermeable sheet 3 are joined. The absorption body and the liquid-impermeable sheet may be joined using, for example, a hot-melt adhesive.

In the embodiment above, the production method of a sanitary napkin is described as an example, but this method can be also applied to the production of other absorbent articles, for example, a pantiliner or an incontinence pad.

DESCRIPTION OF REFERENCE NUMERALS

1: Absorbent article
2: Liquid-permeable sheet
3: Liquid-impermeable sheet
4: Absorption body
5: Center region of absorption body
6: Side sheet
7a: Left compressed groove
7b: Right compressed groove
7a', 7a": Left compressed groove
7b', 7b": Right compressed groove
7c: Front-side compressed groove
7d: Rear-side compressed groove
7e, 7f, 7g: Transverse compressed groove
8: High-compressed part.
9: Low-compressed part
10: Point-like compressed part
11: Slip stopper
12a: Rear end part of front-side compressed groove
12b: Front end part of left compressed groove, front end part of right compressed groove
12c: Rear end part of left compressed groove, rear end part of right compressed groove
12d: Front end part of rear-side compressed groove
13a: Nearly transverse high-compressed groove
13b: Non-transverse high-compressed groove
14: Intermittent part.
CD: Distance between right compressed groove and left compressed groove in the center part of absorbent article
FD: Distance between front end part of the right compressed groove and front end part of the left compressed groove, distance between rear end part of the right compressed groove and rear end part of the left compressed groove Y: Region to which force is applied
Z: Length of intermittent part
W1: Width of compressed groove between a nearly transverse high-compressed groove and a nearly transverse high-compressed groove
W2: Width of compressed groove where a nearly transverse high-compressed part is located

The invention claimed is:

1. An absorbent article having a skin-contact surface side, a longitudinal direction and a widthwise direction, the absorbent article comprising:
   at least a liquid-permeable sheet,
   a liquid-impermeable sheet,
   an absorption body sandwiched between said liquid-permeable sheet and said liquid-impermeable sheet, wherein the absorption body includes a center region having longitudinal side edge parts, a longitudinal front part located forward to the center region, and a longitudinal rear part located backward to the center region, and
   a pair of right and left compressed grooves, on the skin-contact surface side, extending along the longitudinal direction, each of the right and left compressed grooves including
      a middle compressed groove located at least in the corresponding longitudinal side edge part and having a front end part and rear end part,
      a front-side compressed groove located in the longitudinal front part and having a front end part and a rear end part, and
      a rear-side compressed groove located in the longitudinal rear part and having a front end part and rear end part,
   wherein
      the front end part of the middle compressed groove and the rear end part of the front-side compressed groove overlap each other in the widthwise direction, and
      one of the front end part of the middle compressed groove and the rear end part of the front-side compressed groove is located inwardly of the other in the widthwise direction, and runs in parallel with a longitudinal centerline of the absorbent article or outwardly in the widthwise direction,
   wherein
      the rear end part of the middle compressed groove and the front end part of the rear-side compressed groove overlap each other in the widthwise direction, and
      one of the rear end part of the middle compressed groove and the front end part of the rear-side compressed groove is located inwardly of the other in the widthwise direction, and runs in parallel with the longitudinal centerline or outwardly in the widthwise direction,
   wherein
      the front end parts of the middle compressed grooves are separated from each other by a first distance in the widthwise direction,
      the rear end parts of the middle compressed grooves are separated from each other by a second distance in the widthwise direction,
      the middle compressed grooves are separated from each other, at a position configured to correspond to a body fluid discharge port of a wearer, by a third distance in the widthwise direction,
      the third distance is greater than the first and second distances,
      the third distance is from 20 mm to 50 mm,
      a difference between the first and third distances is 5 to 30 mm, and
      a difference between the second and third distances is 5 to 30 mm.

2. The absorbent article according to claim 1, further comprising:
   a transverse compressed groove traversing the longitudinal centerline and provided (i) between the front end parts of said middle compressed grooves or (ii) between the rear end parts of said middle compressed grooves.

3. The absorbent article according to claim 1, further comprising:
   a first transverse compressed groove traversing the longitudinal centerline and arranged between the front end parts of said middle compressed grooves, and
   a second transverse compressed groove traversing the longitudinal centerline and arranged between the rear end parts of said middle compressed grooves,
   wherein the absorbent article has a first rigidity at the first transverse compressed groove and a second rigidity at the second transverse compressed groove, and the second rigidity is lower than the first rigidity.

4. The absorbent article according to claim 1, wherein
   said front-side compressed grooves are connected to form a first curve convex outwardly and forwardly in the longitudinal direction, and
   said rear-side compressed grooves are connected to form a second curve convex outwardly and rearwardly in the longitudinal direction.

5. The absorbent article according to claim 1, further comprising:
   a plurality of point-shaped compressed parts disposed at intervals in a region substantially surrounded by said middle compressed grooves, said front-side compressed grooves and said rear-side compressed grooves.

6. The absorbent article according to claim 1, wherein
   each of said compressed grooves includes a high-compressed part and a low-compressed part,
   each of said compressed grooves has a longitudinal direction and a widthwise direction perpendicular to the longitudinal direction of said compressed groove at any point along said compressed groove, and
   said high-compressed part in each of said compressed grooves includes
      first high-compressed part regions substantially traversing the corresponding compressed groove in the widthwise direction of said compressed groove and disposed at intervals in the longitudinal direction of said compressed groove, and
      second high-compressed part regions not traversing the corresponding compressed groove in the widthwise direction of said compressed groove, and disposed at intervals between said first high-compressed part regions in the longitudinal direction of said compressed groove.

7. The absorbent article according to claim 6, wherein, in each of said compressed grooves, said low-compressed part continuously extends in the longitudinal direction of the compressed groove between the first high-compressed part regions.

8. The absorbent article according to claim 1, wherein the third distance between the middle compressed grooves is at a position where the middle compressed grooves are convex toward each other in the widthwise direction.

9. The absorbent article according to claim 1, further comprising:
- a first transverse compressed groove traversing the longitudinal centerline and arranged between the front end parts of said middle compressed grooves, and
- a second transverse compressed groove traversing the longitudinal centerline and arranged between the rear end parts of said middle compressed grooves.

\* \* \* \* \*